(12) United States Patent
Cho

(10) Patent No.: US 6,174,290 B1
(45) Date of Patent: Jan. 16, 2001

(54) OVULATION PERIOD DETECTING APPARATUS AND OVULATION PERIOD DETECTING METHOD FOR MAMMALS

(75) Inventor: Yukisato Cho, Gunma-ken (JP)

(73) Assignee: Leader Technics Co., Ltd., Gunma-Ken (JP)

( * ) Notice: Under 35 U.S.C. 154(b), the term of this patent shall be extended for 0 days.

(21) Appl. No.: 09/289,363

(22) Filed: Apr. 9, 1999

(30) Foreign Application Priority Data

Apr. 10, 1998 (JP) .................................................. 10-099179
Feb. 19, 1999 (JP) .................................................. 11-042132

(51) Int. Cl.$^7$ ...................................................... A61B 5/00
(52) U.S. Cl. ............................................................. 600/551
(58) Field of Search ................................... 600/547, 551, 600/591

(56) References Cited

FOREIGN PATENT DOCUMENTS

| | | |
|---|---|---|
| 0 339 092 A1 | 11/1989 | (EP) . |
| 61-113437 | 5/1986 | (JP) . |
| 61-137545 | 6/1986 | (JP) . |
| 61-217157 | 9/1986 | (JP) . |
| 1-265948 | 10/1989 | (JP) . |
| 4-220231 | 10/1989 | (JP) . |
| 4-309336 | 10/1992 | (JP) . |
| 7-38856 | 5/1995 | (JP) . |
| 7-87837 | 9/1995 | (JP) . |
| 7-87838 | 9/1995 | (JP) . |
| 7-87840 | 9/1995 | (JP) . |
| 7-87841 | 9/1995 | (JP) . |

*Primary Examiner*—Max Hindenburg
(74) *Attorney, Agent, or Firm*—Weingarten, Schurgin, Gagnebin & Hayes LLP

(57) ABSTRACT

An ovulation period detecting apparatus for mammals is provided comprising: a bar-shaped detecting unit to be inserted in the vagina of a mammal; electrodes arranged on the bar-shaped detecting unit so as to be in contact with the vaginal mucous membrane when the bar-shaped detecting unit is inserted in the vagina of the mammal; pressure detecting means for detecting a pressure at which the electrodes are pressed against the vagina of the mammal; impedance detecting means for applying a voltage across the electrodes and detecting the value of impedance between the electrodes when the pressure detecting means detect a pressure equal to or greater than a prescribed pressure over a prescribed time; and data outputting means for outputting the value of the impedance detected by the impedance detecting means. By means of this ovulation period detecting apparatus, the impedance on the vaginal mucous membrane of a mammal is detected by pressing the electrodes against the vagina of the mammal at a required pressure over a prescribed time to actuate the impedance detecting means for detection. This assures the electrodes to be pressed against the vaginal mucous membrane properly, eliminating the possible intervening of mucus and the like between the electrodes and the vaginal mucous membrane. Thereby, it becomes possible to accurately detect the impedance, based on which semen deposition timings in artificial insemination are determined precisely.

11 Claims, 8 Drawing Sheets

OVULATION PERIOD DETECTING APPARATUS AND OVULATION PERIOD DETECTING METHOD FOR MAMMALS

BACKGROUND OF THE INVENTION

1. Field of the Invention

The present invention relates to an apparatus and a method for detecting an ovulation period of mammals such as hogs, cows, and men.

2. Background Art

Conventionally, ovulation period detecting apparatuses for mammals to be used for predicting the timings of semen deposition include those proposed in Japanese Patent Laid-open Publications Nos.Hei 7-38856, 7-87837, 7-87838, 7-87840, 7-87841, and 7-87842, for example, in which the sodium ion concentration on vaginal mucous membrane is measured on the basis of impedance in inverse proportion thereto to detect the timing of the ovulation period, thereby determining an insemination period or a contraception period.

More specifically, in the case of mammals, e.g., hogs, the equivalent impedance on the vaginal mucous membrane in a non-ovulation period presents such a stable curve as shown in FIG. 9, in which it varies periodically between a zero point and 1.0 k $\Omega$ as time elapses, assuming the equivalent impedance of blood as the zero point. The equivalent impedance starts increasing from 42 to 38 hours before ovulation, approaches the equivalent impedance of water infinitely, becomes generally the same as the equivalent impedance of water just before ovulation, and then decreases sharply to a minimum in two to three hours. Accordingly, the conception ratio of insemination is greatly improved by accurately obtaining the equivalent impedance in insemination-appointed mammals and by depositing of preserved semen at appropriate timings selected for the type of the preserved semen.

However, it is hard to actually obtain fine impedance data, as shown in FIG. 9, in daily routines at a ranch. That is, since the impedance is measured in such a condition that a plurality of electrodes provided on the extremity of a bar-shaped detecting unit are pressed against the vagina and a voltage is applied to the electrodes, the lack or unstableness of a force for pressing the electrodes against the vagina causes the possible intervening of urine, inflammatory exudate, air, mucus, and the like between the electrodes and the vaginal mucous membrane, which gives rise to a problem in that exact and precise data can not be obtained. Therefore, the accurate measurement of the impedance on the vaginal mucous membrane is need.

Besides, the impedance is measured in every mating season on every objective mammal at regular intervals, e.g., a few hours from approximately 40 hours before ovulation, to store data with a time-variation as shown in FIG. 9, for the reason that the timing of ovulation period is predicted and determined on the basis of the stored data. Accordingly, the amount of data on respective objective mammals becomes enormous, which gives rise to a problem in that the data collection is hand- and time-binding as well as burdensome and labor-requiring.

SUMMARY OF THE INVENTION

In the view of the foregoing, an object of the present invention is to provide an apparatus and a method being capable of accurately measuring impedance for determining semen deposition timings in artificial insemination. Besides, another object of the present invention is to provide an apparatus and a method being capable of saving labors and time for the measuring.

The foregoing objects and other objects of the present invention have been achieved by the provision of an ovulation period detecting apparatus for mammals comprising: a bar-shaped detecting unit to be inserted in the vagina of a mammal; a plurality of electrodes arranged on the bar-shape detecting unit so as to be in contact with the vaginal mucous membrane when the bar-shaped detecting unit is inserted in the vagina of the mammal; pressure detecting means for detecting a pressure at which the plurality of electrodes are pressed against the vagina of the mammal; impedance detecting means for applying a voltage across the plurality of electrodes and detecting the value of impedance between the plurality of electrodes when the pressure detecting means detect a pressure equal to or greater than a prescribed pressure over a prescribed time; and data outputting means for outputting the value of the impedance detected by the impedance detecting means.

Besides, the foregoing objects and other objects of the present invention have been achieved by the provision of an ovulation period detecting method for mammals comprising the steps of: pressing a plurality of electrodes of an ovulation period detecting apparatus against the vagina of a mammal at a pressure equal to or greater than a prescribed pressure over a prescribed time, the aforesaid ovulation period detecting apparatus for mammals comprising a bar-shaped detecting unit to be inserted in the vagina of a mammal, the aforesaid plurality of electrodes arranged on the bar-shaped detecting unit so as to be in contact with the vaginal mucous membrane when the bar-shaped detecting unit is inserted in the vagina of the mammal, impedance detecting means for applying a voltage across the aforesaid plurality of electrodes and detecting the value of impedance between the aforesaid plurality of electrodes, and data outputting means for outputting the value of the impedance detected by the aforesaid impedance detecting means; actuating the aforesaid impedance detecting means to detect the value of the impedance between the aforesaid plurality of electrodes; and outputting the value of the impedance via the aforesaid data outputting means.

In addition, the foregoing objects and other objects of the present invention have been achieved by the provision of an an ovulation period detecting apparatus for mammals comprising: a bar-shaped detecting unit to be inserted in the vagina of a mammal; a plurality of electrodes arranged on the bar-shape detecting unit so as to be in contact with the vaginal mucous membrane when the bar-shaped detecting unit is inserted in the vagina of the mammal; voltage generating means for applying a voltage across the aforesaid plurality of electrodes; impedance detecting means for detecting the value of impedance on the aforesaid vaginal mucous membrane between the aforesaid plurality of electrodes having the voltage applied by the voltage generating means; measured data storing means for sorting by objective mammal and storing measured data of the values of the impedance on the aforesaid vaginal mucous membrane detected by the impedance detecting means; and data outputting means for outputting by objective mammal the measured data stored in the measured data storing means in accordance with the measuring time of the measured data.

Moreover, the foregoing objects and other objects of the present invention have been achieved by the provision of an ovulation period detecting apparatus as described above, further comprising automatic storing means for obtaining a rate of change in values of the impedance on the vaginal mucous membrane detected by the impedance detecting means, and storing into the measured data storing means a value of the impedance at the moment where the rate of change has become equal to or smaller than a prescribed set value.

Furthermore, the foregoing objects and other objects of the present invention have been achieved by the provision of an ovulation period detecting means as described above, wherein the automatic storing means further comprises an indicating function for indicating the completion of the measurement on storing into the measured data storing means the value of the impedance at the moment where the rate of change in the values of the impedance on the vaginal mucous membrane detected by the impedance detecting means has become equal to or smaller than the prescribed set value.

Furthermore, the foregoing objects and other objects of the present invention have been achieved by the provision of an ovulation period detecting apparatus as previously described, further comprising: standard data storing means for storing standard data on the time-variations of the impedance on the vaginal mucous membrane over a period from an unfertilizable period to a fertilizable period; and ovulation period prediction outputting means for comparing the standard data stored in the standard data storing means with a value of the impedance detected by the impedance detecting means to predict and output an ovulation period of the objective mammal.

Furthermore, the foregoing objects and other objects of the resent invention have been achieved by the provision of an ovulation period detecting method for mammals comprising the steps of: detecting values of impedance on the vaginal mucous membrane of objective mammals by means of an ovulation period detecting apparatus for mammals comprising a bar-shaped detecting unit to be inserted in the vagina of a mammal, a plurality of electrodes arranged on the bar-shape detecting unit so as to be in contact with the vaginal mucous membrane when the bar-shaped detecting unit is inserted in the vagina of the mammal, voltage generating means for applying a voltage across the aforesaid plurality of electrodes, impedance detecting means for detecting a value of impedance on the aforesaid vaginal mucous membrane between the aforesaid plurality of electrodes having the voltage applied by the voltage generating means, measured data storing means for sorting by objective mammal and storing measured data of the values of the impedance on the aforesaid vaginal mucous membrane detected by the impedance detecting means, and data outputting means for outputting by objective mammal the measured data stored in the aforesaid measured data storing means in accordance with the measuring time of the measured data; storing the detected measured data into the aforesaid measured data storing means; and predicting by objective mammal an ovulation period on the basis of the measured data stored in the aforesaid measured data storing means.

Furthermore, the foregoing objects and other objects of the present invention have been achieved by the provision of an ovulation period detecting method for mammals as previously described, wherein: the aforesaid ovulation period detecting apparatus further comprises automatic storing means; and the automatic storing means obtain a rate of change in values of the impedance detected by the impedance detecting means, and store into the measured data storing means a value of the impedance, as measured data, at the moment where the rate of change has become equal to or smaller than a prescribed set value.

Furthermore, the foregoing objects and other objects of the present invention have been achieved by the provision of an ovulation period detecting method as previously described, wherein the completion of the measurement is indicated on storing into the measured data storing means the value of the impedance at the moment where the rate of change in the values of the impedance detected by the impedance detecting means has become equal to or smaller than the prescribed set value.

Furthermore, the foregoing objects and other objects of the present invention have been achieved by the provision of an ovulation period detecting method for mammals as previously described wherein: the aforesaid ovulation period detecting apparatus further comprises standard data storing means for storing standard data on the time-variations of the impedance detected by the impedance detecting means, and ovulation period prediction outputting means for comparing the standard data stored in the aforesaid standard data storing means with values of the impedance detected by the impedance detecting means to predict and output an ovulation period of an objective mammal; and an ovulation period of an objective mammal is predicted by the aforesaid ovulation period prediction outputting means on the basis of the standard data stored in the aforesaid standard data storing means.

As the foregoing description apparently shows, according to the invention's ovulation period detecting apparatus and method, it becomes possible to accurately measure the values of impedance on the vaginal mucous membrane, based on which the timings of semen deposition in artificial insemination are determined. Therefore, semen can be deposited without an error in timing, greatly improving the conception ratio as compared with the conventional cases.

Besides, ovulation periods are accurately predicted by comparing the measured values of impedance on the vaginal mucous membrane with the standard data; therefore, no error occurs in timing of semen deposition. Moreover, the provision of the several storing means allows the saving of labors in the data collecting.

The nature, principle and utility of the present invention will become more apparent from the following detailed description when read in conjunction with the accompanying drawings.

DETAILED DESCRIPTION OF THE PREFERRED EMBODIMENTS

[First embodiment]

Figure 1:
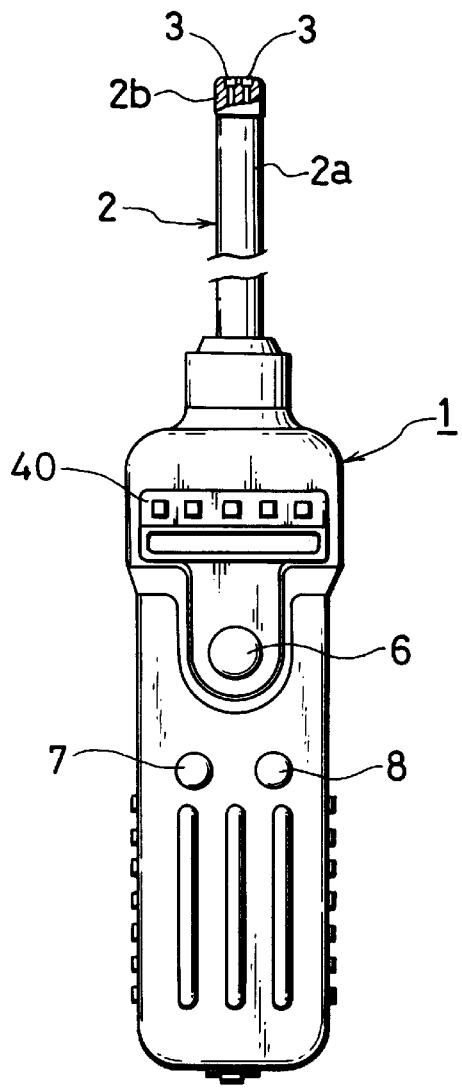
FIG. 1 is an explanatory diagram showing a first embodiment f the present invention.
Figure 2:
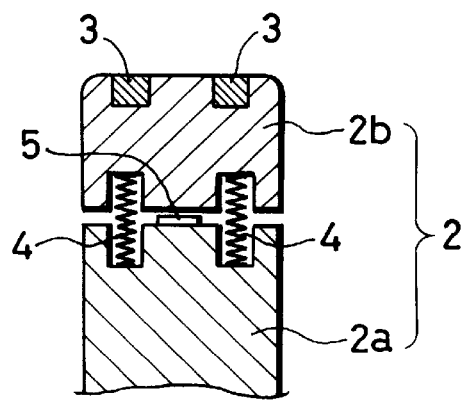
FIG. 2 is an explanatory diagram showing a part of the same.

Hereinafter, a first embodiment of the present invention will be described mainly with reference to FIGS. 1 to 6. As shown in FIGS. 1 and 2, an ovulation period detecting apparatus in this first embodiment has an external configuration comprising a grip body 1, and a bar-shaped detecting unit 2 projecting from the grip body 1 and to be inserted into a vagina of a mammal. On the top of a base 2a of the bar-shaped detecting unit 2 is provided an extremity 2b having a pair of electrodes 3 arranged to be flushed to or slightly projecting from the end portion thereof.

The base 2a and the extremity 2b of the bar-shaped detecting unit 2 are connected via elastic members 4 such as coil springs, which are embedded at the ends thereof into the respective opposing end surfaces of the base 2a and the extremity 2b. A load cell 5 is arranged on the end surface of the base portion 2a to interpose between the opposing end surfaces, so as to enable the detection of a pressure at which the extremity 2b is pressed against the vaginal wall while being held at the grip body 1.

The grip body 1 comprises a measurement starting switch 6, a pressure indicating lamp 7, and a measurement indicating lamp 8. Besides, as shown in FIG. 3, the grip body 1 further comprises such conventionally known members as: voltage generating means 10 for applying a voltage across the electrodes 3; sodium ion concentration detecting means 30 including impedance detecting means 20 for detecting the impedance between the voltage-applied electrodes 3; and indicating means 40 as data outputting means for indicating the condition of vaginal mucous membrane on the basis of the detected impedance.

This indicating means 40 indicates a semen deposition period (fertilizable period) before ovulation, and an unfertilizable period in which ovulation does not occur. For example, a value generally equaling to the equivalent impedance of water such as drinking water is taken as a set value just before ovulation; and when the equivalent impedance on the aforesaid vaginal mucous membrane generally equals to the set value, the indicating means 40 indicates that the mammal is in the semen deposition period (fertilizable period) before ovulation. Then, a value generally equaling to the equivalent impedance of the blood of the mammal is taken as a set value for non-ovulation, for example; and when the equivalent impedance on the aforesaid vaginal mucous membrane generally equals to this set value, the indicating means 40 indicates that the mammal is in an unfertilizable period in a non-ovulation period.

Figure 3:
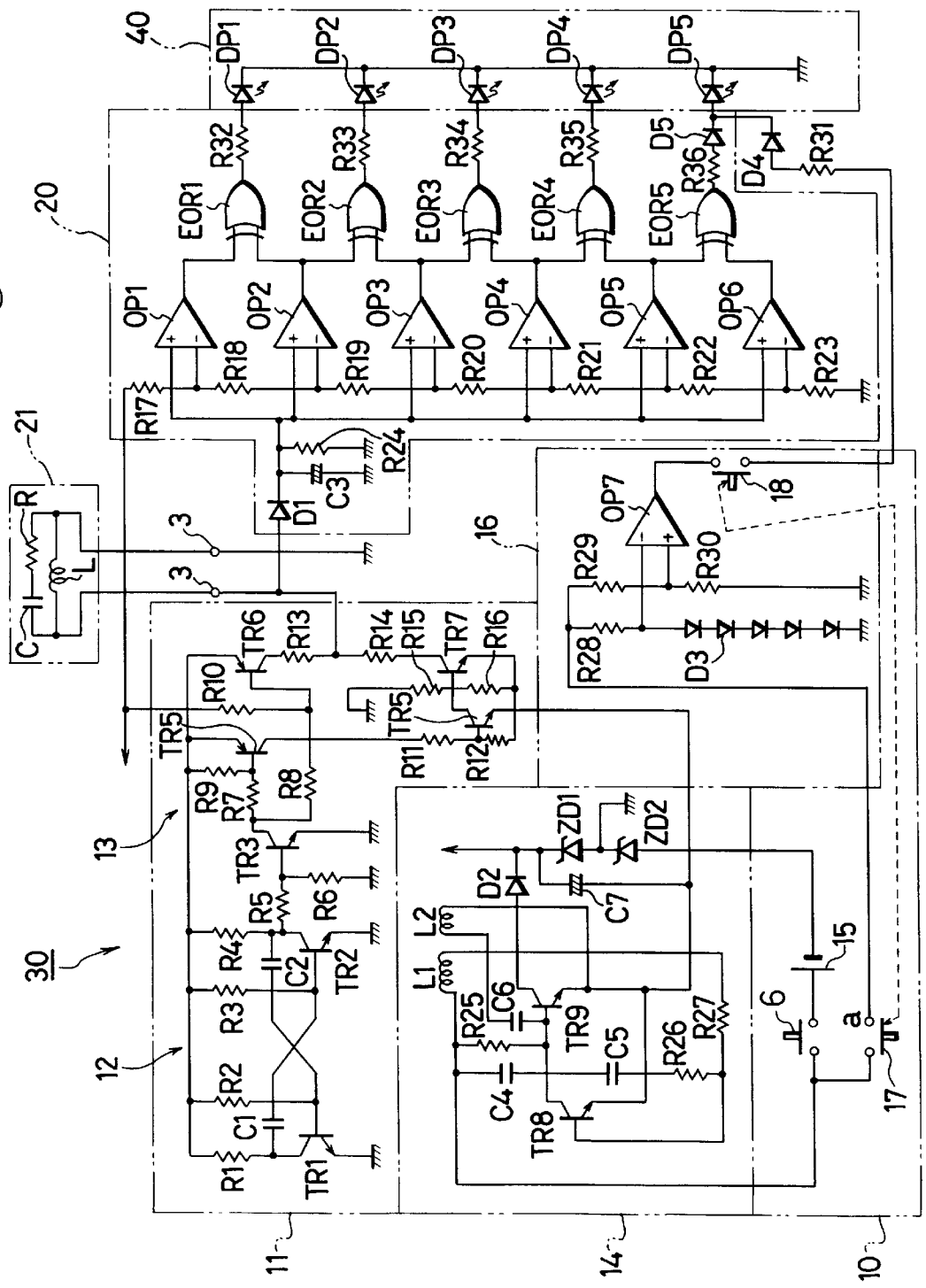
FIG. 3 is a circuit diagram of the same.

More specifically, as shown in FIG. 3, the aforesaid voltage generating means 10 comprise ac power generating means 11, boosting means 14, and voltage comparing means 16. The aforesaid ac power generating means 11 comprise an astable multivibrator 12 and a positive-negative pulse amplifier 13. The aforesaid astable multivibrator 12 comprises, as principal components, transistors TR1 and TR2, resistors R1 to R4, and capacitors C1 and C2. The aforesaid positive-negative pulse amplifier 13 comprises transistors TR3 to TR7 and resistors R5 to R16 for amplifying pulses outputted by the aforesaid astable multivibrator 12.

The aforesaid boosting means 14 include an inverter circuit for raising a supply voltage supplied by a power battery 15 up to required voltage. The boosting means 14 comprise amplifying transistors TR8 and TR9, and further comprise capacitors C4 to C7, resistors R25 to R27, coils L1 and L2, a diode D2, and Zener diodes ZD1 and ZD2 for applying the supply voltage given by the aforesaid power battery 15 to the transistors TR8 and TR9 for boosting. The positive electrodes of the Zener diode ZD1 and the aforesaid diode D2 are connected to the resistor R10 in the aforesaid ac power generating means 11 and to the resistor R17 in the impedance detecting means 20 so as to receive the boosted voltage and a current.

The aforesaid impedance detecting means 20 comprise a plurality of voltage comparators for detecting the impedance level of an impedance equivalent circuit 21 of an objective portion (the vaginal mucous membrane) by means of an ac voltage applied across the aforesaid electrodes 3, and are activate by the closing of the measurement starting switch 6 on the grip body 1. The impedance equivalent circuit 21 consists of a capacitor C, a resistor R, and a coil L. The aforesaid indicating means 40 has light emitting diodes DP1 to DP5 respectively corresponding to impedance levels determined by the aforesaid impedance detecting means 20 to indicate the corresponding impedance levels.

In order to determine the impedance level of the impedance equivalent circuit 21 on the basis of a voltage signal which is developed across the aforesaid electrodes 3 and given through the diode D1, the aforesaid impedance detecting means 20 comprise resistors R17 to R23 for dividing a voltage applied thereto by the aforesaid boosting means 14, and operational amplifiers OP1 to OP6 for comparing the divided voltages with the aforesaid voltage signal. Besides, the impedance detecting means 20 further comprise exclusive OR circuits EOR1 to EOR5 for performing exclusive OR operations, in order to generate light emission signals for the light emitting diodes DP1 to DP 5 provided in the aforesaid indicating means 40 on the basis of the output signals of the respective operational amplifiers OP1 to OP6.

Elements including a capacitor C3 and a resistor R24 are connected to the positive terminal of the aforesaid diode D1 to stabilize the input voltage signal given to the operational amplifiers OP1 to OP6.

The aforesaid voltage comparing means 16 is used for checking (diagnosing) an under voltage of the aforesaid power battery 15, and is actuated by the closing of a power check switch 17. The aforesaid voltage comparing means 16 comprise resistors R28 to R30, a diode series D3, and an operational amplifier OP7 for comparing the voltages divided by these resistors R28 to R30 and diode series D3, to diagnose the voltage of the aforesaid power battery 15 inputted through the power check switch 17.

The result of the comparative check in the aforesaid voltage comparing means 16 is supplied, as a decision signal, to the light emitting diode DPS provided in the aforesaid indicating means 40 through a contact 18 switched concurrently with the aforesaid power check switch 17. By this means, the aforesaid light emitting diode P5 is driven to emit light in accordance with the decision signal.

The output signal of the aforesaid operational amplifier OP7 is given through a resistor R31 and a diode D4 to the aforesaid light emitting diode DP5. A diode D5 is provided at the junction point to the aforesaid diode D4 so as to prevent the backward application of the aforesaid decision signal to the aforesaid exclusive OR circuit EOR5.

Voltage dividing resistors R32 to R36 are connected to the respective output terminals of the aforesaid exclusive OR circuits EOR1 to EOR5 to divide the light emission signals applied to the respective light emission terminals of the aforesaid light emitting diodes DP1 to DP5.

The sum of the resistances of the voltage dividing resistors R18 to R23 in the aforesaid impedance detecting means 20 is provided to be slightly smaller than the impedance across the electrodes 3 in the drinking water for the objective mammal, such as tap water and spring water, or in the water showing an electric resistance equivalent thereto. Since a normal body temperature of a hog, for example, is 38.5° C., the sum of the resistances of the voltage dividing resistors R18 to R23 is on the order of 2.14 kΩ, which is slightly smaller that the equivalent impedance across the electrodes 3 immersed in water at a temperature of 38.5° C. Concretely, the sum of the resistances is set so that the aforesaid light emitting diode DP1 is lighted up when the aforesaid electrodes 3 are immersed in water at a temperature of 38.5° C.

The resistance of the aforesaid voltage dividing resistor R23 is set to be generally the same as the equivalent impedance of the blood of the objective mammal, which is, for example, a value on the order of 0.78 kΩ for a hog. Concretely, the resistance of the voltage dividing resistor R23 is set so that the aforesaid light emitting diode DP1 is turned off when the aforesaid electrodes 3 are immersed in the blood.

The sum of the resistances of the aforesaid voltage dividing resistors R19 to R23 is set to be the same as the equivalent impedance on the vaginal mucous membrane of the objective mammal at an appropriate period for the depositing of chilled semen, which is, for example, a value on the order of 1.88 kΩ for the hog.

The sum of the resistances of the aforesaid voltage dividing resistors R20 to R23 is set to be equal to the equivalent impedance on the vaginal mucous membrane of the objective mammal at an appropriate period for the depositing of frozen semen, which is, for example, a value on the order of 1.644 kΩ for the hog.

The sum of the resistances of the aforesaid voltage dividing resistors R21 to R23 is set to be generally the same as the maximum equivalent impedance on the vaginal mucous membrane of the objective mammal during an unfertilizable period in a non-ovulation period, which is, for example, a value on the order of 1.00 kΩ for the hog.

The sum of the resistances of the aforesaid voltage dividing resistors R22 and R23 is set to be generally the same as the lower half of the equivalent impedance on the vaginal mucous membrane of an objective mammal during an unfertilizable period in the non-ovulation period, which is, for example, a value on the order of 0.867 kΩ for the hog.

When the electrodes 3 on the extremity 2a of the bar-shaped detecting unit 2 are pressed against the vaginal mucous membrane and the measurement starting switch 6 on the grip body 1 is operated, a voltage appearing in accordance with the impedance of the impedance equivalent circuit 21 between the electrodes 3 is inputted through the diode D1 to the respective noninverting input terminals of the operational amplifiers OP1 to OP6. Meanwhile, the voltages divided by the resistors R17 to R23 are applied to the inverting input terminals of these operational amplifiers OP1 to OP6, respectively. Hereby, the comparisons are performed between the voltage given from the impedance equivalent circuit 21 and the voltages respectively applied to the operational amplifiers OP1 to OP6, and the results of the comparisons are respectively inputted to the exclusive OR circuits EOR1 to EOR5.

Here, the voltages applied to the inverting input terminals of the respective operational amplifiers OP1 to OP6 increase stepwise according to the resistances of the resistors R23 to R17 in the order of the operational amplifiers OP6 to OP1. The exclusive OR circuits EOR1 to EOR5 respectively obtain the exclusive ORs of the outputs of the adjacent pairs of the operational amplifiers OP1 to OP6. Consequently, one of the light emitting diodes DP1 to DP5 is lighted up according to the value of the impedance equivalent circuit 21.

As described above, the sum of the resistances of the voltage dividing resistors R18 to R23 in the impedance detecting means 20 is generally the same as the impedance of water, and the sum of the resistances of the voltage dividing resistors R19 to R23 is equal to the equivalent impedance on the vaginal mucous membrane in an appropriate condition for the disposing of chilled semen. Accordingly, the lighting-up of the light emitting diode DP1 indicates an appropriate period for the disposing of frozen semen, and the lighting-up of the light emitting diode DP2 indicates an appropriate period for the disposing of chilled semen.

In the cases where the impedance across the electrodes 3 equals to the equivalent impedance of water, both the output signals of the operational amplifiers OP1 and OP2 are inputted to the exclusive OR circuit EOR1, thereby turning off the light emitting diode DP1. Utilizing this operation, the electrodes 3 can be immersed in water to check (diagnose) the ovulation period detecting apparatus.

The sum of the resistances of the voltage dividing resistances R21 to R23 in the impedance detecting means 20 is equal to the maximum impedance of the impedance equivalent circuit 21 on the vaginal mucous membrane of the objective mammal in its unfertilizable period in a non-ovulatory condition; therefore, the lighting-up of the light emitting diode DP4 or DP5 indicates the unfertilizable period.

The light emitting diode DP4 represents a high-level impedance in the unfertilizable period and the light emitting diode DP5 represents a low-level impedance in the unfertilizable period. This enables the determination on whether or not "the ovulation is approaching," or on whether or not "the ovulation has already occurred," in the case where the objective mammal is in its mating season. Here, the light emitting diode DP3 indicates an unclear intermediate period between the fertilizable period and the unfertilizable period, so-called "gray zone."

The resistance of the voltage dividing resistor R23 in the impedance detecting means 20 is set to be slightly greater than the impedance of the blood of the objective mammal; thus, the immersion of the electrodes 3 in the objective mammal's blood turns the light emitting diode DP5 off.

In other words, the electrodes 3 can be immersed into a liquid equivalent to water or the objective mammal's blood in impedance, as described above, to check the ovulation period detecting apparatus on its zero level.

Figure 4:
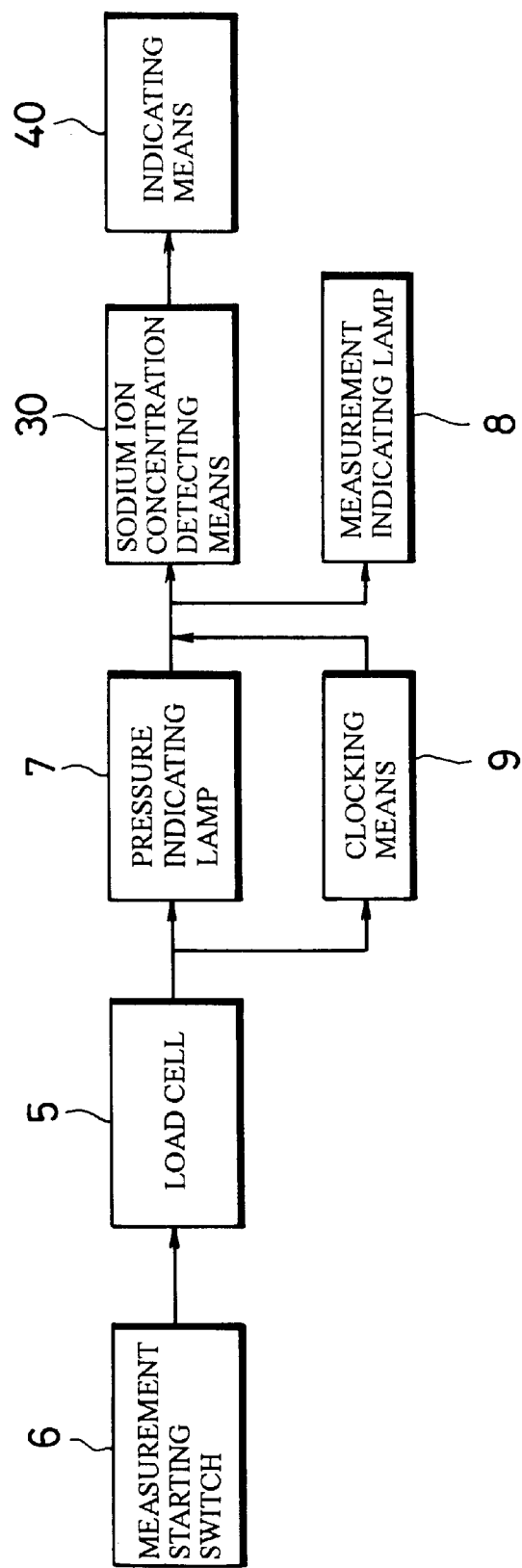
FIG. 4 is a block diagram of the same.

Here, the lack or unstableness of a force for pressing the electrodes 3 against the vagina, however, causes the possible intervening of urine, inflammatory exudate, air, mucus, and the like between the electrodes 3 and the vaginal mucous membrane, thereby disturbing the obtaining of accurate data. Accordingly, as shown in FIG. 4, clocking means 9 such as a clock IC are provided in the grip body 1, so that the sodium ion concentration detecting means 30 are actuated to detect the impedance on the vaginal mucous membrane between the electrodes 3 after the load cell 5 has detected pressure equal to or greater than a prescribed pressure over a prescribed time.

Figure 5:
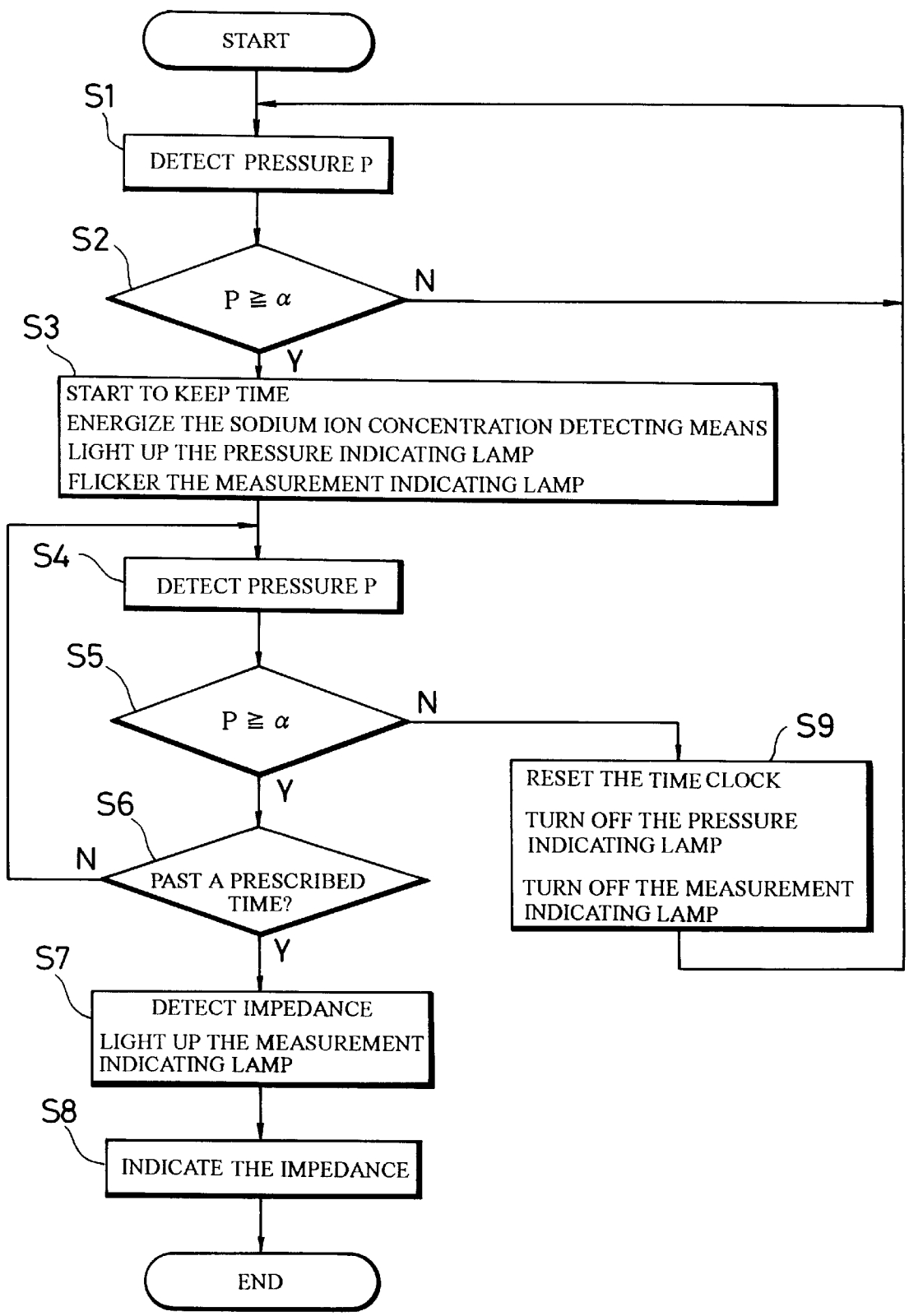
FIG. 5 is a control flow chart of the same.

More specifically, in this ovulation period detecting apparatus according to the present invention, a control program as shown in FIG. 5, for example, is stored in a not-shown control storage unit. For a start, being held at the grip body 1, the bar-shaped detecting unit 2 is inserted in the vagina of a mammal. The electrodes 3 provided on the extremity 2b of the bar-shaped detecting unit 2 are pressed against the vaginal mucous membrane, and the measurement starting switch 6 on the grip body 1 is pushed to operate (the switch may be operated before the insertion of the bar-shaped detecting unit 2 into the vagina). At step S1, the load cell 5 detects a pressure P at which the electrodes 3 are pressed against the vaginal wall. At step S2, it is determined whether or not the pressure P is equal to or greater than a prescribed pressure α.

When it is determined to be YES in step S2, the processing proceeds to step S3, in which the clocking means 9 start to keep a clock time and the pressure indicating lamp 7 is lighted to indicate that the electrodes 3 are pressed against the vaginal wall with a pressure equal to or greater than the prescribed pressure α. Besides, the sodium ion concentration detecting means 30 are energized to stabilize the detecting circuits electrically, and the measurement indicating lamp 8 is flickered to indicate that he measurement is in preparation. When it is determined to be NO in step S2, the processing returns to step S1.

At step S4, the load cell 5 newly detects the pressure P at which the electrodes 3 are pressed against the vaginal wall. At step S5, it is determined whether or not the pressure P is equal to or greater than the prescribed pressure α. When it is determined to be YES, the processing proceeds to step S6, in which it is determined whether or not the clock time kept by the clocking means 9 reaches a prescribed time (60 seconds, for example). When it is determined to be NO in step S5, the processing moves to step S9, in which the pressure indicating lamp 7 and the measurement indicating lamp 8 are turned off to indicate that the electrodes 3 are not pressed against the vaginal wall at a pressure equal to or greater than the prescribed pressure α, and that the preparation for measurement is discontinued. In this case, the clock time kept by the clocking means 9 is reset, and the processing returns to step S1.

The determination of NO in step S6 moves the processing back to step S4. Conversely, the determination of YES in step S6 proceeds the processing to step S7, in which the sodium ion concentration detecting means 30 detect the impedance on the vaginal mucous membrane between the electrodes 3, and the measurement indicating lamp 8 is lighted to indicate the completion of the measurement. Then, the light emitting diode corresponding to the detected impedance is lighted up, so that the measurement result is indicated on the indicating means 40.

Figure 6:
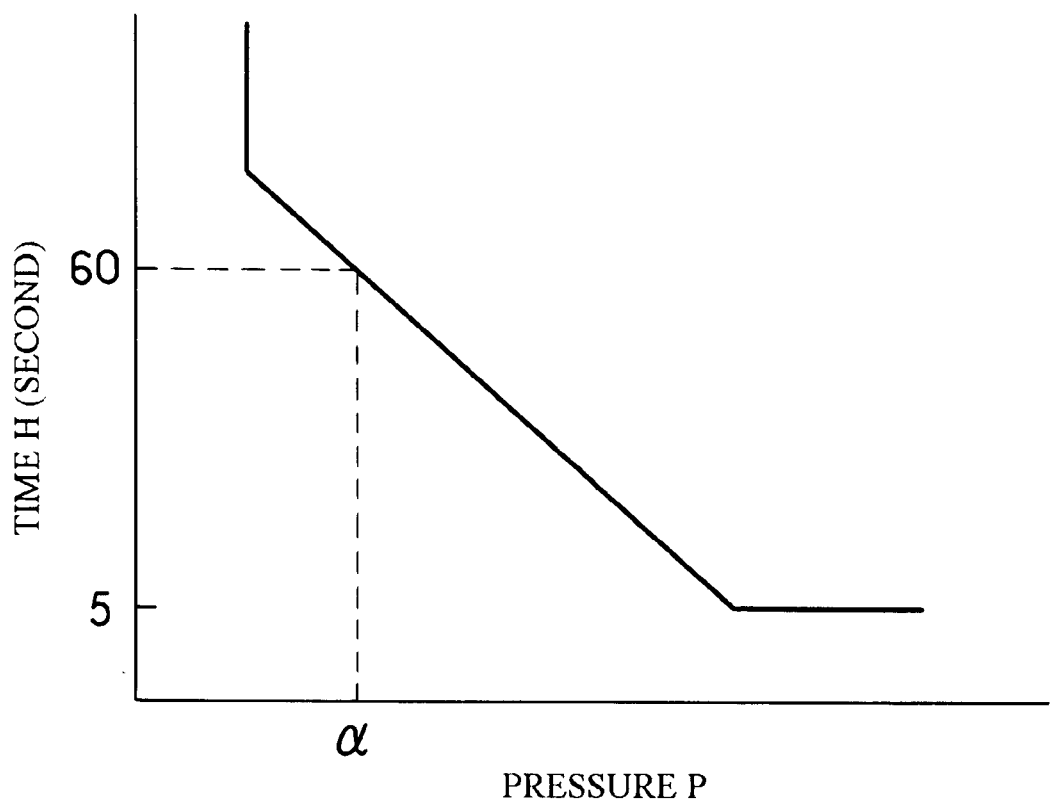
FIG. 6 is an explanatory diagram showing the relation between the time and pressure for pressing electrodes against a vagina.

According to the ovulation period detecting apparatus of the present invention, the impedance on the vaginal mucous membrane between the electrodes 3 is measured after the electrodes 3 are pressed against the vaginal wall at a pressure equal to or greater than a prescribed pressure over a prescribed time, as described above. Here, the pressure P for pressing the electrodes 3 against the vaginal wall and a time H for the pressing are set as shown in FIG. 6, for example, in which the time H is decreased with an increase of the pressure 2, but is secured to be equal to or greater than 5 seconds, favorably equal to or greater than 10 seconds, for any increase of the pressure P. As a result, urine, inflammatory exudate, air, mucus, and the like are eliminated from under the electrodes 3, the measurement is performed after the wait for the perfect contact of the electrodes 3 with the vaginal mucous membrane, and thereby stable impedance data can be obtained.

Accordingly, the conception rate of artificial insemination is greatly improved as compared with the cases where conventional apparatuses and methods of this type are used.

Note that the sodium ion concentration detecting means 30 may be energized after the electrodes are pressed against the vaginal wall at a pressure equal to or greater than the prescribe pressure α for a prescribed time, e.g., 52 seconds, and that the impedance across the electrodes 3 may be measured after a prescribed time in wait for the electrical stability of the detecting circuits, which is, for example, 8 seconds after the energizing. Even in this case, it is apparent to detect whether the electrodes 3 are pressed against the vaginal wall at a pressure equal to or greater than the prescribed pressure during the wait for the electrical stability of the detecting circuits.

Besides, in place of the measurement indicating lamp 8, a LCD may be provided to digitally display the remaining time required for the pressing of the electrodes 3 against the vaginal wall at a prescribed pressure; or, there may be provided a plurality of LEDs, which are sequentially turned off by prescribed interval, e.g., every 5 seconds to indicate the remaining time.

Moreover, the indicating means 40 may indicate the impedance only in a period in which the electrodes 3 are pressed with a pressure equal to or greater than the prescribe pressure α, or only for a prescribed time, e.g., 10 seconds. A switch may be provided to turn off the indication.

While the measurement indicating lamp 8 is switched from flickering to lighting and the value of the impedance is indicated on the indicating means 40 at the completion of the measurement, electronic beep sounds and vibrations may also be used for indicating the completion of the measurement, for example.

In addition, the ovulation period detecting apparatus may be arranged so that: measured data on the time-variation of the equivalent impedance on the vaginal mucous membrane of objective mammals over a period from a non-ovulation period to an ovulation period detected by the impedance detecting means 20 are sorted by objective mammal and stored; and the stored measured data are outputted by objective mammal to other displaying means of the apparatus itself, a PC, and the like in accordance with the measuring time of the objective mammal.

In this case, the data may be displayed in the form of images, scrolls, and graphs, for example.

Moreover, the ovulation period detecting apparatus may be constituted so as to store a plurality of data of different types as standard data and to compare the value of the objective mammal's impedance detected by the impedance detecting means 20 with the standard data to predict and output an ovulation period of the objective mammal similar to the aforesaid standard data.

In this constitution, when types of the variations of the impedance are determined and filed on the basis of the detailed measured data on an objective mammal measured in the first artificial insemination, the ovulation period for the objective mammal can be predicted and determined easily and accurately in subsequent artificial inseminations by performing the measurement only once or a few times in appropriate periods before ovulation.

[Second embodiment]

Figure 7:
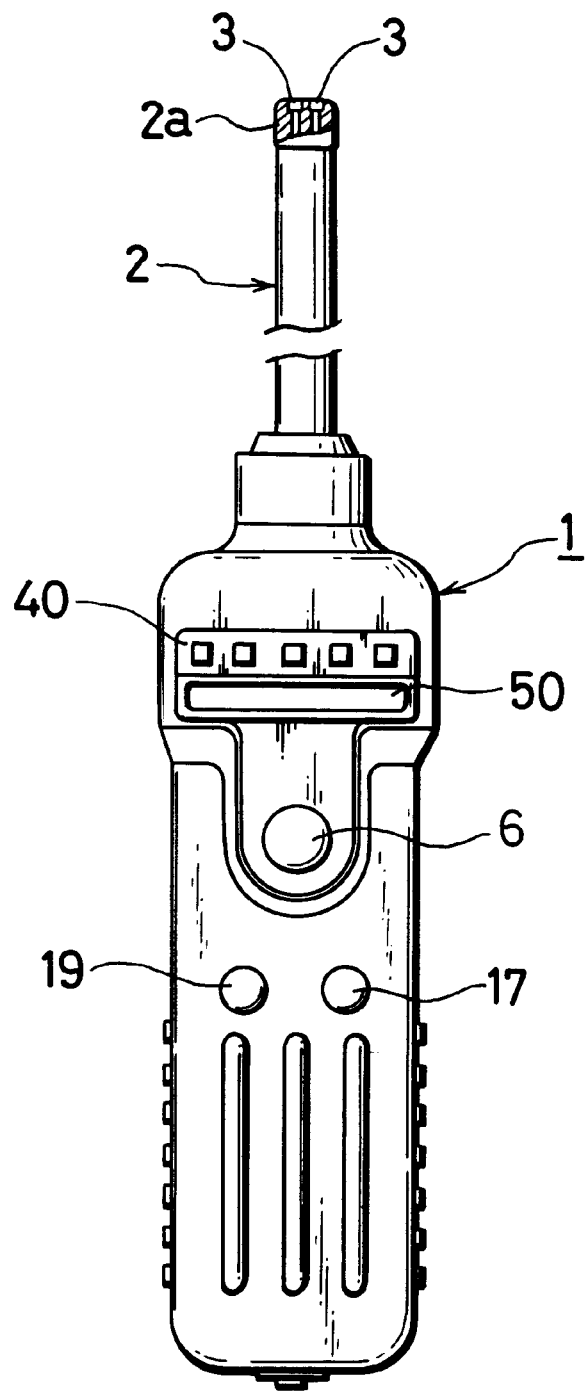
FIG. 7 is an explanatory diagram showing a second embodiment of the present invention.

Next, a second embodiment of the present invention will be described mainly with reference to FIGS. 7 and 8. As shown in FIG. 7, an ovulation period detecting apparatus of the second embodiment has the same external configuration as the aforesaid apparatus shown in FIG. 1. The grip body 1 thereof comprises the electric circuit shown in FIG. 3, the power check switch 17 for checking an under voltage of the power battery 15, and an after-mentioned automatic measurement starting switch 19 and screen display unit 50. The grip body 1 further comprises the measurement starting switch 6 and the indicating means 40 functioning as described above.

Note that this ovulation period detecting apparatus does not comprise the pressure indicating lamp 7, the measurement indicating lamp 8, or the load sell 5, which are provided in the aforesaid ovulation period detecting apparatus shown in FIG. 1.

Figure 8:
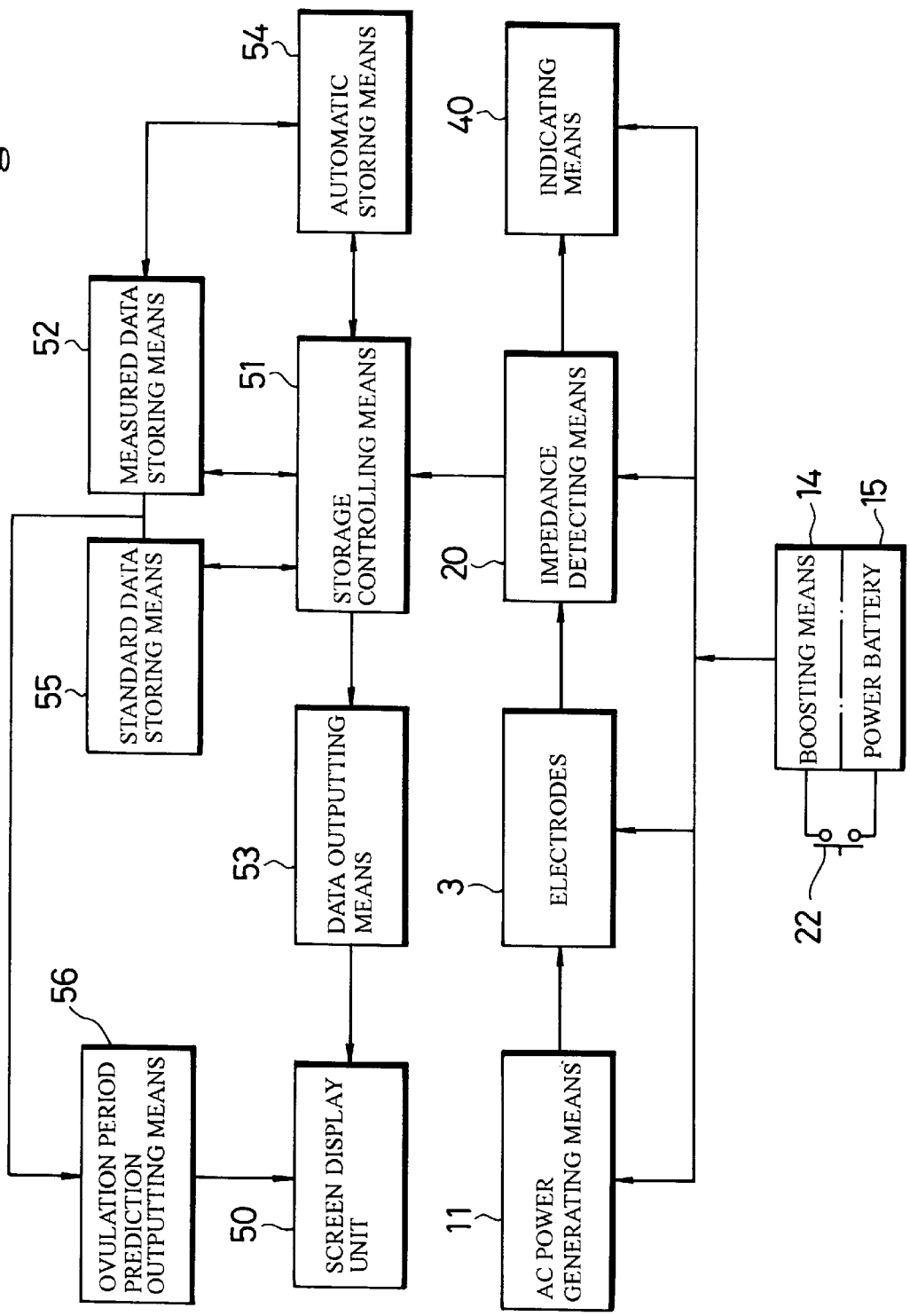
FIG. 8 is a block diagram of the same.
Figure 9:
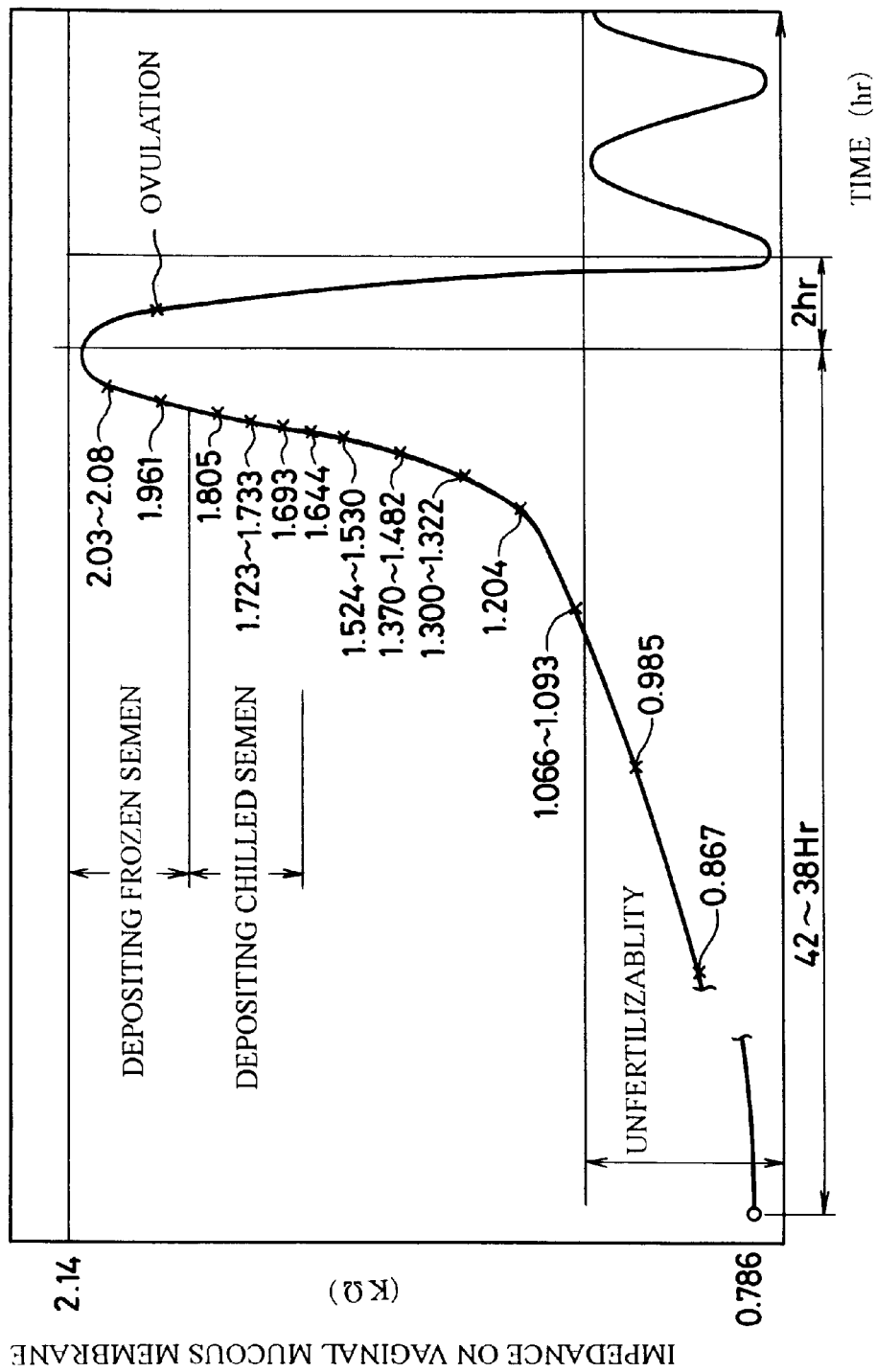
FIG. 9 is an explanatory diagram showing measured data on the time-variation of the impedance on hog's vaginal mucous membrane over a period from a non-ovulation period to an ovulation period.

As shown in FIG. 8, this ovulation period detecting apparatus further comprises storage controlling means 51, measured data storing means 52, and data outputting means 53, and is arranged so that: the aforesaid impedance detecting means 20 detects measured data on the time-variation of the equivalent impedance on the vaginal mucous membrane of objective mammals over a period from a non-ovulation period to an ovulation period thereof; the measured data are sorted by objective mammal and stored in the measured data storing means 52 via the storage controlling means 51 connected to the aforesaid impedance detecting means 20; and the measured data stored in the measured data storing means 52 are outputted by objective mammal via the data outputting means 53 in accordance with the measuring time of the objective mammal.

The aforesaid measured data storing means 52 is capable of storing the measured data on 100 objective mammals, for example. the measured data outputted by the data outputting means 53 may be displayed directly on the screen display unit 50 of the apparatus itself, or may be displayed on a PC and the like via terminal connection. The screen display unit 50 displays the data in the form of images, scrolls, and graphs, for example.

Between the aforesaid impedance detecting means 20 and the aforesaid measured data storing means 52 are connected automatic storing means 54 via the aforesaid storage controlling means 51. By means of the automatic storing means 54, rates of change in the impedance on the vaginal mucous membrane of objective mammals detected by the aforesaid impedance detecting means 20 are obtained, and values of the impedance at time points where the rates of change become equal to or smaller than a prescribed set value are stored, as measured data, into the aforesaid measured data storing means 52. The completion of the measurement is indicated by the lighting of light emitting diodes, for example. In this connection, the completion of the measurement may be indicated by electronic beep sounds or vibrations.

The aforesaid automatic storing means 54 is actuated for the operation as described above by closing the automatic measurement starting switch 19 provided on the aforesaid grip body 1.

Here, as a modification, the aforesaid automatic storing means 54 may be omitted, and a manual storing switch may be provided on the aforesaid grip body 1. In this case, after having confirmed that changes in the impedance displayed as measured data on the screen display unit 50 of the aforesaid grip body 1 are faded, the manual storing switch is operated so that the impedance data, which the aforesaid impedance detecting means 20 are detecting at the moment, are stored into the aforesaid measured data storing means 52 as measured data.

The aforesaid storage controlling means 51 are further connected to standard data storing means 55. The standard data storing means 55 store, as standard data, a plurality of, e.g., three to five of different types of data on the impedance variations for an objective mammal over a period from an unfertilizable period to a fertilizable ovulation period thereof, which are detected by the aforesaid impedance detecting means 20 and stored in the measured data storing means 52. Ovulation period prediction outputting means 56 compare the standard data and the value of the impedance on the objective mammal detected by the aforesaid impedance detecting means 20 to predict an ovulation period of the objective mammal and output it to the screen display unit 50.

Here, mode changing means, which are not shown in the drawings, are provided to change the display mode of the screen display unit 50. Besides, the standard data to be compared with the impedance on the objective mammal detected by the impedance detecting means 20 can be designated using a not-shown type designating switch.

In brief, the ovulation period detecting apparatus of the present embodiment can predict and determine the ovulation period for each object mammal according to the values of the impedance on the object mammal detected by the aforesaid impedance detecting means 20 and the measured data of similar type stored in the aforesaid standard data storing means 55.

Consequently, when types of the variations of the impedance are determined and filed on the basis of the detailed measured data on the respective objective mammals measured in the first artificial insemination, the ovulation period for each objective mammal can be predicted and determined easily and accurately in subsequent artificial inseminations by performing the measurement only once or a few times in appropriate periods before ovulation.

In this connection, in the ovulation period detecting apparatus for such mammals that the time-variations of the impedance have little individual differences, the standard data storing means 55 is arranged to store only one set of standard data.

It should be noted that an ovulation period detecting apparatus according to the present invention is naturally applicable for contraception and diagnosis of uterus.

While there has been described what are at present considered to be preferred embodiments of the invention, it will be understood that various modifications may be made thereto, and it is intended that the appended claims cover all such modifications as fall within the true spirit and scope of the invention.

What is claimed is:

1. An ovulation period detecting apparatus for mammals comprising:

a bar-shaped detecting unit to be inserted in a vagina of a mammal;

a plurality of electrodes arranged on the bar-shape detecting unit so as to be in contact with a vaginal mucous membrane when the bar-shaped detecting unit is inserted in the vagina of the mammal;

voltage generating means for applying a voltage across said plurality of electrodes;

impedance detecting means for detecting a value of impedance on said vaginal mucous membrane between said plurality of electrodes having the voltage applied by the voltage generating means;

measured data storing means for sorting by objective mammal and storing measure data of the values of the impedance on said vaginal mucous membrane detected by the impedance detecting means;

data outputting means for outputting by objective mammal the measured data stored in the measured data storing means in accordance with the measuring time of the measured data and automatic storing;

and automatic storing means for obtaining a rate of change in values of the impedance on the vaginal mucous membrane detected by the impedance detecting means, and storing into the measured data storing means a value of the impedance at the moment where the rate of change has become equal to or smaller than prescribed set value.

2. The ovulation period detecting means according to claim 1, wherein the automatic storing means comprises an indicating function for indicating the completion of the measurement on storing into the measured data storing means the value of the impedance at the moment where the rate of change in the values of the impedance on the vaginal mucous membrane detected by the impedance detecting means has become equal to or smaller than the prescribed set value.

3. The ovulation period detecting apparatus according to claim 1, said apparatus comprising:

standard data storing means for storing standard data on time-variations of the impedance on the vaginal mucous membrane over a period from an unfertilizable period to a fertilizable period; and ovulation period prediction outputting means for comparing the standard data stored in the standard data storing means with a value of the impedance detected by the impedance detecting means to predict and output an ovulation period of the objective mammal.

4. The ovulation period detecting apparatus according to claim 2, said apparatus comprising:

standard data storing means for storing standard data on time-variations of the impedance on the vaginal mucous membrane over a period from an unfertilizable period to a fertilizable period; and ovulation period prediction outputting means for comparing the standard data stored in the standard data storing means with a value of the impedance detected by the impedance detecting means to predict and output an ovulation period of the objective mammal.

5. An ovulation period detecting apparatus for mammals comprising:

a bar-shaped detecting unit to be inserted in a vagina of a mammal;

a plurality of electrodes arranged on the bar-shape detecting unit so as to be in contact with a vaginal mucous membrane when the bar-shaped detecting unit is inserted in the vagina of the mammal;

voltage generating means for applying a voltage across said plurality of electrodes;

impedance detecting means for detecting a value of impedance on said vaginal mucous membrane between said plurality of electrodes having the voltage applied by the voltage generating means;

measured data storing means for sorting by objective mammal and storing measure data of the values of the impedance on said vaginal mucous membrane detected by the impedance detecting means;

data outputting means for outputting by objective mammal the measured data stored in the measured data storing means in accordance with the measuring time of the measured data;

standard data storing means for storing standard data on time-variations of the impedance on the vaginal mucous membrane over a period from an unfertilizable period to a fertilizable period; and ovulation period prediction outputting means for comparing the standard data stored in the standard data storing means with a value of the impedance detected by the impedance detecting means to predict and output an ovulation period of the objective mammal.

6. An ovulation period detecting method for mammals, comprising the steps of:

detecting values of impedance on a vaginal mucous membrane of objective mammals by means of an ovulation period detecting apparatus for mammals comprising a bar-shaped detecting unit to be inserted in a vagina of a mammal, a plurality of electrodes arranged on the bar-shape detecting unit so as to be in contact with the vaginal mucous membrane when the bar-shaped detecting unit is inserted in the vagina of the mammal, voltage generating means for applying a voltage across said plurality of electrodes, impedance detecting means for detecting a value of impedance on said vaginal mucous membrane between said plurality of electrodes having the voltage applied by the voltage generating means, measured data storing means for sorting by objective mammal and storing measured data of the values of the impedance on said vaginal mucous membrane detected by the impedance detecting means, and data outputting means for outputting by objective mammal the measured data stored in said measured data storing means in accordance with the measuring time of the measured data;

storing the detected measured data into said measured data storing means; and predicting by objective mammal an ovulation period on the basis of the measured data stored in said measured data storing means.

7. The ovulation period detecting method for mammals according to claim 6, wherein:

said ovulation period detecting apparatus comprises automatic storing means; and the automatic storing means obtain a rate of change in values of the impedance detected by the impedance detecting means, and store into the measured data storing means a value of the impedance, as measured data, at the moment where the rate of change has become equal to or smaller than a prescribed set value.

8. The ovulation period detecting method according to claim 7, wherein the completion of the measurement is indicated on storing into the measured data storing means the value of the impedance at the moment where the rate of change in the values of the impedance detected by the impedance detecting means has become equal to or smaller than the prescribed set value.

9. The ovulation period detecting method for mammals according to claim 6, wherein:

said ovulation period detecting apparatus comprises standard data storing means for storing standard data on the time-variations of the impedance detected by the impedance detecting means, and ovulation period prediction outputting means for comparing the standard data stored in said standard data storing means with values of the impedance detected by the impedance detecting means to predict and output an ovulation period of an objective mammal; and an ovulation period of an objective mammal is predicted by said ovulation period prediction outputting means on the basis of the standard data stored in said standard data storing means.

10. The ovulation period detecting method for mammals according to claim 7, wherein:

said ovulation period detecting apparatus comprises standard data storing means for storing standard data on the time-variations of the impedance detected by the impedance detecting means, and ovulation period prediction outputting means for comparing the standard data stored in said standard data storing means with values of the impedance detected by the impedance detecting means to predict and output an ovulation period of an objective mammal; and an ovulation period of an objective mammal is predicted by said ovulation period prediction outputting means on the basis of the standard data stored in said standard data storing means.

11. The ovulation period detecting method for mammals according to claim 8, wherein:

said ovulation period detecting apparatus comprises standard data storing means for storing standard data on the time-variations of the impedance detected by the impedance detecting means, and ovulation period prediction outputting means for comparing the standard data stored in said standard data storing means with values of the impedance detected by the impedance detecting means to predict and output an ovulation period of an objective mammal; and an ovulation period of an objective mammal is predicted by said ovulation period prediction outputting means on the basis of the standard data stored in said standard data storing means.

* * * * *